US009084898B2

(12) United States Patent
Li

(10) Patent No.: US 9,084,898 B2
(45) Date of Patent: Jul. 21, 2015

(54) METHOD AND DEVICE FOR PROVIDING ANTI-TACHYARRHYTHMIA THERAPY

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/569,208

(22) Filed: Aug. 8, 2012

(65) Prior Publication Data

US 2012/0296383 A1 Nov. 22, 2012

Related U.S. Application Data

(62) Division of application No. 11/382,120, filed on May 8, 2006, now Pat. No. 8,255,049.

(51) Int. Cl.
*A61N 1/365* (2006.01)
*A61N 1/362* (2006.01)
*A61N 1/36* (2006.01)
*A61N 1/39* (2006.01)

(52) U.S. Cl.
CPC ............ *A61N 1/3621* (2013.01); *A61N 1/3605* (2013.01); *A61N 1/36114* (2013.01); *A61N 1/36564* (2013.01); *A61N 1/3962* (2013.01)

(58) Field of Classification Search
CPC ............ A61N 1/3605; A61N 1/36114; A61N 1/3622; A61N 1/3962; A61B 5/0402
USPC ..................... 607/6, 9, 14, 18, 116, 117, 118; 600/508, 509
See application file for complete search history.

(56) References Cited

U.S. PATENT DOCUMENTS

| 5,203,326 | A | 4/1993 | Collins |
| 5,405,363 | A | 4/1995 | Kroll et al. |
| 5,578,061 | A | 11/1996 | Stroetmann et al. |

(Continued)

FOREIGN PATENT DOCUMENTS

| EP | 0688577 | 12/1995 |
| EP | 0688578 | 12/1995 |

(Continued)

OTHER PUBLICATIONS

"U.S. Appl. No. 11/382,120, Advisory Action mailed Jan. 31, 2012", 3 pgs.

(Continued)

*Primary Examiner* — Eric D. Bertram
*Assistant Examiner* — Pamela M Bays
(74) *Attorney, Agent, or Firm* — Schwegman Lundberg & Woessner, P.A.

(57) ABSTRACT

Various system embodiments comprise at least one sensor input adapted to receive at least one sensed signal associated with a tachyarrhythmia, a feature set extractor adapted to extract at least two features from the at least one sensed signal associated with the tachyarrhythmia, a feature set generator adapted to form a feature set using the at least two features extracted by the feature set extractor, at least one generator adapted for use to selectively apply an anti-tachycardia pacing (ATP) therapy and a neural stimulation (NS) therapy, and a controller adapted to respond to the feature set. The controller is adapted to initiate the NS therapy when the feature set corresponds to criteria for applying the NS therapy to modify the tachyarrhythmia, and initiate the ATP therapy to terminate the modified tachyarrhythmia. Other aspects and embodiments are provided herein.

20 Claims, 11 Drawing Sheets

(56) References Cited

U.S. PATENT DOCUMENTS

| | | | |
|---|---|---|---|
| 5,662,689 A | 9/1997 | Elsberry et al. | |
| 5,697,953 A | 12/1997 | Kroll et al. | |
| 5,817,131 A | 10/1998 | Elsberry et al. | |
| 5,827,326 A | 10/1998 | Kroll et al. | |
| 5,836,976 A | 11/1998 | Min et al. | |
| 5,893,881 A | 4/1999 | Elsberry et al. | |
| 5,954,752 A | 9/1999 | Mongeon et al. | |
| 5,957,956 A | 9/1999 | Kroll et al. | |
| 6,134,470 A * | 10/2000 | Hartlaub | 607/14 |
| 6,292,695 B1 | 9/2001 | Webster, Jr. et al. | |
| 6,567,691 B1 | 5/2003 | Stadler | |
| 6,571,125 B2 | 5/2003 | Thompson | |
| 6,611,713 B2 | 8/2003 | Schauerte | |
| 6,647,292 B1 | 11/2003 | Bardy et al. | |
| 6,668,191 B1 | 12/2003 | Boveja | |
| 6,721,597 B1 | 4/2004 | Bardy et al. | |
| 6,931,278 B1 | 8/2005 | Kroll et al. | |
| 6,952,610 B2 | 10/2005 | Ostroff et al. | |
| 6,988,003 B2 | 1/2006 | Bardy et al. | |
| 7,039,459 B2 | 5/2006 | Bardy et al. | |
| 7,043,299 B2 | 5/2006 | Erlinger et al. | |
| 7,069,080 B2 | 6/2006 | Bardy et al. | |
| 7,076,294 B2 | 7/2006 | Bardy et al. | |
| 7,218,964 B2 | 5/2007 | Hill et al. | |
| 7,225,017 B1 | 5/2007 | Shelchuk | |
| 7,245,967 B1 | 7/2007 | Shelchuk | |
| 7,321,793 B2 | 1/2008 | Ben Ezra et al. | |
| 8,244,350 B2 | 8/2012 | Zhang et al. | |
| 8,255,049 B2 | 8/2012 | Li | |
| 2002/0035335 A1 | 3/2002 | Schauerte | |
| 2002/0042630 A1 | 4/2002 | Bardy et al. | |
| 2002/0068958 A1 | 6/2002 | Bardy et al. | |
| 2002/0082658 A1 | 6/2002 | Heinrich et al. | |
| 2002/0103510 A1 | 8/2002 | Bardy et al. | |
| 2002/0111601 A1 | 8/2002 | Thompson | |
| 2002/0147407 A1 * | 10/2002 | Seim | 600/513 |
| 2003/0078623 A1 * | 4/2003 | Weinberg et al. | 607/9 |
| 2003/0181951 A1 | 9/2003 | Cates | |
| 2003/0191403 A1 | 10/2003 | Zhou et al. | |
| 2003/0212436 A1 | 11/2003 | Brown | |
| 2003/0236558 A1 | 12/2003 | Whitehurst et al. | |
| 2004/0193231 A1 | 9/2004 | David et al. | |
| 2004/0220629 A1 | 11/2004 | Kamath et al. | |
| 2004/0225332 A1 * | 11/2004 | Gebhardt et al. | 607/17 |
| 2004/0254612 A1 | 12/2004 | Ezra et al. | |
| 2005/0065553 A1 | 3/2005 | Ben Ezra et al. | |
| 2005/0131464 A1 | 6/2005 | Heinrich et al. | |
| 2005/0131467 A1 | 6/2005 | Boveja | |
| 2005/0143776 A1 | 6/2005 | Brown | |
| 2005/0187584 A1 | 8/2005 | Denker et al. | |
| 2005/0187585 A1 * | 8/2005 | Mussig et al. | 607/9 |
| 2006/0136001 A1 | 6/2006 | Ortega et al. | |
| 2006/0206154 A1 | 9/2006 | Moffitt et al. | |
| 2006/0253157 A1 | 11/2006 | Libbus et al. | |
| 2007/0100380 A1 | 5/2007 | Fukui | |
| 2007/0179543 A1 | 8/2007 | Ben-David et al. | |
| 2007/0203527 A1 | 8/2007 | Ben-David et al. | |
| 2007/0260283 A1 | 11/2007 | Li | |
| 2008/0046016 A1 | 2/2008 | Ben-David et al. | |
| 2008/0086174 A1 | 4/2008 | Libbus et al. | |
| 2008/0269819 A1 | 10/2008 | Zhou | |
| 2009/0198294 A1 | 8/2009 | Rossing et al. | |
| 2010/0036447 A1 | 2/2010 | Zhang et al. | |

FOREIGN PATENT DOCUMENTS

| | | |
|---|---|---|
| EP | 1304135 | 4/2003 |
| JP | 08038626 | 2/1996 |
| JP | 2004508149 | 3/2004 |
| JP | 2004351122 | 12/2004 |
| JP | 2009536558 | 10/2009 |
| WO | WO-0027474 | 5/2000 |
| WO | WO-0222208 | 3/2002 |
| WO | WO-2004105870 | 12/2004 |
| WO | WO-2006039694 | 4/2006 |
| WO | WO-2006098996 | 9/2006 |
| WO | WO-2006098996 A1 | 9/2006 |
| WO | WO-2006121836 | 11/2006 |
| WO | WO-2007133877 | 11/2007 |
| WO | WO-2007133877 A3 | 11/2007 |
| WO | WO-2008042468 | 4/2008 |

OTHER PUBLICATIONS

"U.S. Appl. No. 11/382,120, Advisory Action mailed Oct. 1, 2010", 6 pgs.

"U.S. Appl. No. 11/382,120, Examiner Interview Summary mailed Aug. 11, 2011", 4 pgs.

"U.S. Appl. No. 11/382,120, Final Office Action mailed Jul. 8, 2010", 12 pgs.

"U.S. Appl. No. 11/382,120, Final Office Action mailed Oct. 28, 2011", 8 pgs.

"U.S. Appl. No. 11/382,120, Non Final Office Action mailed Mar. 30, 2011", 14 pgs.

"U.S. Appl. No. 11/382,120, Non-Final Office Action mailed Nov. 27, 2009", 11 pgs.

"U.S. Appl. No. 11/382,120, Notice of Allowance mailed Apr. 3, 2012", 10 pgs.

"U.S. Appl. No. 11/382,120, PTO Response to Rule 312 Communication mailed Aug. 1, 2012", 2 pgs.

"U.S. Appl. No. 11/382,120, Response filed Mar. 29, 2010 to Non Final Office Action mailed Nov. 27, 2009", 13 pgs.

"U.S. Appl. No. 11/382,120, Response filed Aug. 4, 2011 to Non Final Office Action mailed Mar. 30, 2011", 13 pgs.

"U.S. Appl. No. 11/382,120, Response filed Sep. 8, 2010 to Final Office Action mailed Jul. 8, 2010", 14 pgs.

"U.S. Appl. No. 11/382,120, Response filed Sep. 30, 2009 to Restriction Requirement rnailed Sep. 4, 2009", 10 pgs.

"U.S. Appl. No. 11/382,120, Response filed Dec. 28, 2011 to Final Office Action mailed Oct. 28, 2011", 11 pgs.

"U.S. Appl. No. 11/382,120, Restriction Requirement mailed Sep. 4, 2009", 5 pgs.

"U.S. Appl. No. 11/538,488, Advisory Action mailed Oct. 21, 2011", 3 pgs.

"U.S. Appl. No. 11/538,488, Examiner interview Summary mailed Oct. 20, 2011", 3 pgs.

"U.S. Appl. No. 11/538,488, Final Office Action mailed Feb. 22, 2010", 16 pgs.

"U.S. Appl. No. 11/538,488, Final Office Action mailed Jun. 15, 2011", 6 pgs.

"U.S. Appl. No. 11/538,488, Non Final Office Action mailed Dec. 27, 2010", 8 pgs.

"U.S. Appl. No. 11/538,488, Non-Final Office Action mailed Jun. 29, 2009", 13 pgs.

"U.S. Appl. No. 11/538,488, Non-Final Office Action mailed Oct. 29, 2008", 19 pgs.

"U.S. Appl. No. 11/538,488, Response filed Jan. 29, 2009 to Final Office Action mailed Oct. 29, 2008", 14 pgs.

"U.S. Appl. No. 11/538,488, Response filed Apr. 14, 2011 to Non Final Office Action mailed Dec. 27, 2010", 12 pgs.

"U.S. Appl. No. 11/538,488, Response filed Apr. 27, 2009 to Restriction Requirement mailed Mar. 26, 2009", 9 pgs.

"U.S. Appl. No. 11/538,488, Response filed Jun. 22, 2010 to Final Office Action mailed Feb. 22, 2010", 15 pgs.

"U.S. Appl. No. 11/538,488, Response filed Oct. 14, 2011 to Final Office Action mailed Jun. 15, 2011", 10 pgs.

"U.S. Appl. No. 11/538,488, Response filed Oct. 29, 2009 to Non Final Office Action mailed Jun. 29, 2009", 15 pgs.

"U.S. Appl. No. 11/538,488, Restriction Requirement mailed Mar. 26, 2009", 6 pgs.

"U.S. Appl. No. 12/535,332, Non Final Office Action mailed Sep. 26, 2011", 5 pgs.

"European Application Serial No. 07783811.8, Communication mailed Jun. 17, 2010", 4 pgs.

"European Application Serial No. 07760739.8, Examination Notification Art. 94(3) mailed May 16, 2011", 4.

(56) References Cited

OTHER PUBLICATIONS

"European Application Serial No. 07760739.8, Examination Notification Art. 94(3) Response Filed Oct. 26, 2011", 15 pgs.

"European Serial No. 07783811.8 Office Action Response filed Dec. 16, 2010 to Office Action mailed Jun. 17, 2010", 11 pgs.

"International Application Serial No. PCT/US2007/066741, International Search Report mailed Jan. 30, 2008", 4 pgs.

"International Application Serial No. PCT/US2007/066741, Written Opinion mailed Jan. 30, 2008", 9 pgs.

"Japanese Application Serial No. 2009-509919, Amended Claims filed Feb. 10, 2010", (w/ English Translation of Amended Claims), 11 pgs.

"Japanese Application Serial No. 2009-531494, Amended Claims filed Mar. 31, 2010", (w/ English Translation), 11 pgs.

"Japanese Application Serial No. 2009-531494, Office Action mailed Jul. 9, 2012", (w/ English Translation), 5 pgs.

"PCT Application Serial No. PCT/US2007/068741, Written Opinion mailed Jan. 30, 2008", 8 pgs.

"PCT Application Serial No. PCT/US2007/066741, Written Opinion mailed Jan. 30, 2008", 8 pgs.

Ando, M., et al., "Efferent vagal nerve stimulation protects heart against ischemia-induced arrhythmias by preserving connexin43 protein", Circulation, 112(2), Jul. 12, 2005), 164-70.

Kouakam, C., et al., "Effect of elevated heart rate preceding the onset of ventricular tachycardia on antitachycardia pacing effectiveness in patients with implantable cardioverter defibrillators.", American Journal of Cardiology, 92(1), (Jul. 1, 2003), 26-32.

Murakawa, Y., et al., "Effect of Cervical Vagal Nerve stimulation on Defibrillation Energy: a Possible Adjunct to Efficient Defibrillation", Japanese Heart Journal, 44(1), (Jan. 2003), 91-100.

Shelchuk, A. M. "Optimisation of ICD therapy-DFT how to reduce it?" Europace, vol. 7, No. S1, (2005), 105-106.

Takahashi, N, et al., "Vagal modulation of ventricular tachyarrhythmias induced by left ansae subclaviae stimulation in rabbits", Japanese Heart Journal, 39(4), (Jul. 1998), 503-11.

Vanoli, E., et al., "Vagal Stimulation and Prevention of Sudden Death in Conscious Dogs With a Healed Myocardial Infarction", Circulation Research, 68(5), (May 1991), 1471-1481.

Zamotrinskya. A. V., et al., "Vagal neurostimulation in patients with coronary artery disease.", Auton Neurosci., 88(1-2), (Apr. 12, 2001), 109-16.

"Japanese Application Serial No. 2009-509919, Office Action mailed Jan. 20, 2012", (w/ English Translation), 5 pgs.

"Japanese Application Serial No. 2009-509919, Office Action Response Filed Apr. 10, 2012", W/English Translation, 11 Pgs.

\* cited by examiner

US 9,084,898 B2

METHOD AND DEVICE FOR PROVIDING ANTI-TACHYARRHYTHMIA THERAPY

CLAIM OF PRIORITY

This application is a division of and claims the benefit of priority under 35 U.S.C. §120 to Li, U.S. patent application Ser. No. 11/382,120, entitled "METHOD AND DEVICE FOR PROVIDING ANTI-TACHYARRHYTHMIA THERAPY," filed on May 8, 2006, now issued as U.S. Pat. No. 8,255,049, which is hereby incorporated by reference herein in its entirety.

FIELD OF THE INVENTION

This application relates generally to the treatment of heart disease and more particularly, to systems, devices and methods to treat cardiac arrhythmias with electrical stimulation.

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. Contractions of the myocardium provide these pumping functions. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony, which efficiently pumps the blood. Blocked or abnormal electrical conduction or deteriorated myocardial tissue causes dysynchronous contraction of the heart, resulting in poor hemodynamic performance, including a diminished blood supply to the heart and the rest of the body. Heart failure occurs when the heart fails to pump enough blood to meet the body's metabolic needs.

Tachyarrhythmias are abnormal heart rhythms characterized by a rapid heart rate. Examples of tachyarrhythmias include supraventricular tachycardias (SVT's) such as atrial tachycardia (AT), and atrial fibrillation (AF), and the more dangerous ventricular tachyarrhythmias which include ventricular tachycardia (VT) and ventricular fibrillation (VF). Abnormal ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Most abnormal ventricular rhythms exhibit an abnormal QRS complex in an electrocardiogram because the depolarization spreads from the excitatory focus or point of re-entry directly into the myocardium rather than through the normal ventricular conduction system. Ventricular tachycardia is typically characterized by distorted QRS complexes that occur at a rapid rate, while ventricular fibrillation is diagnosed when the ventricle depolarizes in a chaotic fashion with no identifiable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of cardiac rhythm management (CRM) devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Cardioversion/defibrillation consumes a relatively large amount of stored power from the battery and can cause patient discomfort. It is desirable, therefore, to terminate a tachyarrhythmia whenever possible without using shock therapy. Devices have therefore been programmed to use ATP to treat lower rate tachycardias and to use cardioversion/defibrillation shocks to terminate fibrillation and certain high rate tachycardias.

SUMMARY

Described herein is a device, system and method for treating atrial or ventricular tachyarrhythmias which, in addition to ATP and shock therapy, employs neural stimulation. The neural stimulation may be parasympathetic stimulation or sympathetic inhibition.

Various aspects of the present subject matter relate to a system. Various system embodiments comprise at least one sensor input adapted to receive at least one sensed signal associated with a tachyarrhythmia, a feature set extractor adapted to extract at least two features from the at least one sensed signal associated with the tachyarrhythmia, a feature set generator adapted to form a feature set using the at least two features extracted by the feature set extractor, at least one generator adapted for use to selectively apply an anti-tachycardia pacing (ATP) therapy and a neural stimulation (NS) therapy, and a controller adapted to respond to the feature set. The controller is adapted to initiate the NS therapy when the feature set corresponds to criteria for applying the NS therapy to modify the tachyarrhythmia, and initiate the ATP therapy to terminate the modified tachyarrhythmia.

Various system embodiments comprise at least one sensor input adapted to receive at least one sensed signal associated with a tachyarrhythmia, a feature set extractor adapted to extract at least two features from the at least one sensed signal associated with the tachyarrhythmia, a feature set generator adapted to form a feature set using the at least two features extracted by the feature set extractor, at least one generator adapted for use to selectively apply a shock therapy, an ATP therapy, and a neural stimulation therapy, and a controller adapted to respond to the feature set. The controller is adapted to initiate the shock therapy when the feature set corresponds to criteria for applying the shock therapy, initiate the ATP therapy when the feature set corresponds to criteria for applying the ATP therapy, and initiate the NS therapy when the feature set corresponds to criteria for applying the NS therapy.

Various aspects of the present subject matter relate to a method. According to various embodiments of the method, a NS therapy is applied to modify a ventricular tachycardia (VT), and an ATP therapy is applied to terminate the modified VT.

According to various embodiments of the method, at least one sensed signal associated with a tachyarrhythmia is received, at least two features are extracted from the at least one sensed signal associated with the tachyarrhythmia and a feature set is formed using the at least two features. A shock therapy is provided when the feature set corresponds to criteria for applying the shock therapy. An ATP therapy is provided when the feature set corresponds to criteria for applying the ATP therapy. An NS therapy is provided when the feature set corresponds to criteria for applying the NS therapy to modify the tachyarrhythmia to be amenable to the ATP therapy.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
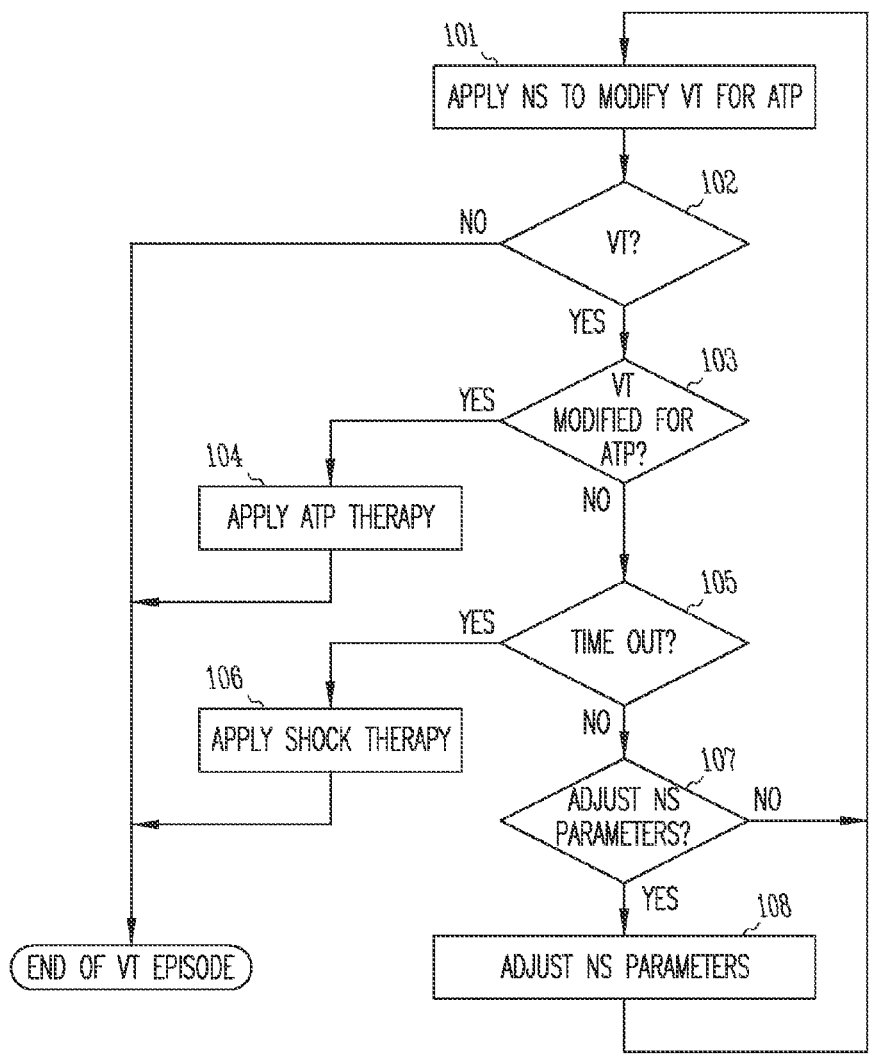
FIG. 1 illustrates an anti-tachycardia therapy, according to various embodiments of the present subject matter.

The following detailed description of the present subject matter refers to accompanying drawings which show, by way of illustration, specific aspects and embodiments in which the present subject matter may be practiced. These embodiments are described in sufficient detail to enable those skilled in the art to practice the present subject matter. Other embodiments my be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results bradycardia, vasodilation, and inhibition of vasopressin release. Among many other factors, decreased parasympathetic or vagal tone or increased sympathetic tone is associated with various arrhythmias genesis, including ventricular tachycardia and atrial fibrillation. In ICDs, efficacy of anti-tachycardia therapy such as ATP is also significantly affected by sympathetic/parasympathetic activation. It was reported that sinus tachycardia preceding VT onset and lack of beta blockers independently predicted higher ATP failure and acceleration. The circadian pattern of ATP success may also suggest that increased sympathetic activation plays a role in ATP therapy efficacy.

The present disclosure relates to an implantable device with the capability of sensing the presence of a tachyarrhythmia and terminating the arrhythmia with a combination of neural stimulation, ATP, and/or high-voltage shocks. Embodiments of the present subject matter directly determine the appropriate therapy for the tachyarrhythmia using a composite set of features associated with the tachyarrhythmia. The number of features in the feature set is at least two features associated with the feature set. For example, various embodiments map the tachyarrhythmia to the appropriate therapy using the feature set.

Embodiments of the present subject matter use neural stimulation to condition the tachyarrhythmia to make it more amenable to ATP therapy. Neural stimulation, in the form of sympathetic inhibition or parasympathetic activation, decreases myocardial excitability and conduction time. The neural stimulation thus changes the characterizations of the tachycardia to that treatable by ATP. As identified above, ATP has conventionally been used to treat lower rate tachycardias, while shocks have been used to terminate higher rate tachycardias and fibrillation. Embodiments of the present subject matter provide a method to improve the ATP efficacy on a broader spectrum of VTs such as those with higher rate and/or not very stable rhythms. According to the present subject matter, neurostimulation (NS) is used to modify the VT characteristics (e.g. slow down the rate) and restore the hemodynamic function to some extent (e.g. increase filling) when the VTs are deemed inappropriate to be treated by immediate ATP. This preconditioning of the arrhythmia changes the VT characteristics to make the VT more amendable to ATP therapy, therefore improving the overall success of ATP on wider array of VTs.

According to an embodiment, a VT is detected (e.g. falling in a rate zone and sustained), and an N-dimensional feature set R is constructed, where $R=\{R_1, R_2, \ldots, R_N\}$. Each element $R_i$ in the R set is a feature extracted either from electrical signals such as intracardiac EGM, or from the signals recorded by one or more sensors such as an accelerometer, a pressure sensor, an impedance sensor, and the like. The features from these sensor signals are measures or estimates of the hemodynamic stability during the VT. The composite features in R are then mapped to one of the following decisions: "Deliver ATP"; "Deliver Shock"; "Deliver NS". The mapping is implemented as a set of algorithms.

"Deliver NS" is selected if the VT rhythms are characterized by moderately fast rate and unstable rhythm, and modest hemodynamic compromise. Electrical pulses are generated by the device and delivered through an NS lead to the vagal nerve in the surface of certain blood vessel where stimulation electrode is positioned. The appropriate NS parameters can be selected using the feature set. If the VT persists following MS but modified such that it meets the "Deliver ATP" criteria, ATP is delivered. It is expected that applying NS to precondition the tachyarrhythmia for an ATP therapy will allow the ATP to terminate a number of VTs that would have been rendered to either shock therapy which can cause patient discomfort or ATP which could fail or even accelerate the rhythm without the NS preconditioning.

Anti-Tachycardia Therapy Embodiments

As provided above, a collected feature set can be mapped to determine whether to treat the tachycardia with ATP therapy, shock therapy, or neural stimulation. If the mapped feature set indicates that the ATP therapy is not likely to be successful, embodiments of the present subject matter apply neural stimulation (NS) to stimulate the parasympathetic system and/or inhibit the sympathetic system, and then determine if the resulting tachycardia is amenable to ATP therapy.

FIG. 1 illustrates an anti-tachycardia therapy, according to various embodiments of the present subject matter. At 101, neural stimulation is applied to modify the VT for ATP. It is possible that the neural stimulation may terminate the VT. Thus, at 102, it is determined whether the VT is still present. If it is determined that the VT is still present, it is determined at 103 whether the VT has been modified such that the modified VT can be successfully treated with ATP. If it has, the process proceeds to 104 to deliver an ATP therapy to terminate the VT. If the VT has not been modified for ATP, the process proceeds to 105 to determine whether a time out has occurred. The time out is a period of time or a number of neural stimulation attempts to modify the VT for ATP therapy. If a time out occurs at 105, the process proceeds to 106 to apply a shock therapy, such as a defibrillation or cardioversion therapy, to terminate the VT. If a time out has not occurred at 105, the process proceeds to 107 to determine whether the neural stimulation parameters should be adjusted. If the NS parameters are not to be adjusted at 107, the process returns to 101 to deliver the neural stimulation. If the NS parameters are to be adjusted at 107, the process proceeds to adjust the neural stimulation parameters at 108, and then returns to 101 to deliver the neural stimulation. As discussed below with respect to FIG. 2, NS parameters can be adjusted to adjust the intensity of the neural stimulation therapy.

Figure 2:
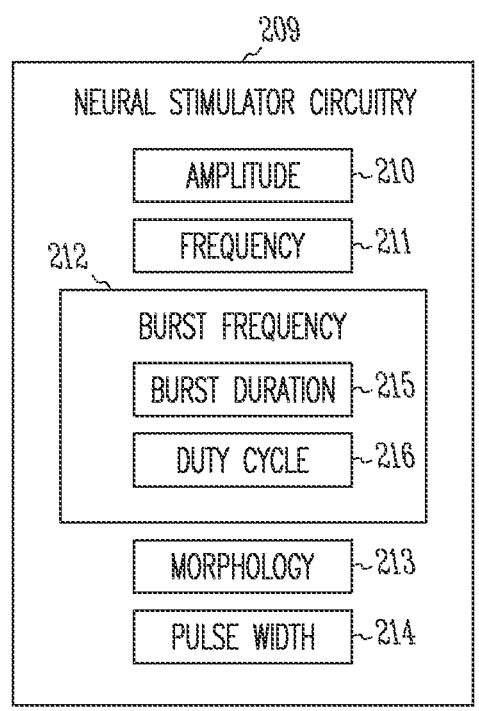
FIG. 2 illustrates a neural stimulator, and further illustrates various neural stimulation parameters that can be adjusted to adjust a neural stimulation therapy, according to various embodiments of the present subject matter.

FIG. 2 illustrates a neural stimulator, and further illustrates various neural stimulation parameters that can be adjusted to adjust a neural stimulation therapy, according to various embodiments of the present subject matter. According to various embodiments, the neural stimulator 209 includes modules to set or adjust any one or any combination of two or more of the following pulse features delivered to the neural stimulation electrode(s) or transducer(s): the amplitude 210 of the stimulation pulse, the frequency 211 of the stimulation pulse, the burst frequency 212 of the pulse, the wave morphology 213 of the pulse, and the pulse width 214. Examples of neural stimulation electrodes include nerve cuffs, and intravascularly-fed electrodes to transvascularly stimulate a neural target. Examples of neural transducers include ultrasound, magnetic and light transducers used to stimulate a neural target. The illustrated burst frequency pulse feature 212 includes burst duration 215 and duty cycle 216, which can be adjusted as part of a burst frequency pulse feature or can be adjusted separately. For example, a burst frequency can refer to the number of bursts per minute. Each of these bursts has a burst duration (an amount of time bursts of stimulation are provided) and a duty cycle (a ratio of time where stimulation is provided to total time). Thus, by way of example and not limitation, six bursts can be delivered during a one minute stimulation time (burst duration), where the length (pulse width) of each burst is five seconds and the time period between bursts is five seconds. In this example, the burst frequency is six bursts per minute, the stimulation time or burst duration is 60 seconds, and the duty cycle is 50% ((6 bursts×5 sec./burst)/60 seconds). Additionally, the duration of one or more bursts can be adjusted without reference to any steady burst frequency. For example, a single stimulation burst of a predetermined burst duration or a pattern of bursts of predetermined pulse width(s) and burst timing can be provided in response to a sensed signal. Furthermore, the duty cycle can be adjusted by adjusting the number of bursts and/or adjusting the duration of one or more bursts, without requiring the bursts to be delivered with a steady burst frequency. Examples of wave morphology include a square wave, triangle wave, sinusoidal wave, and waves with desired harmonic components to mimic white noise such as is indicative of naturally-occurring baroreflex stimulation.

Figure 3:
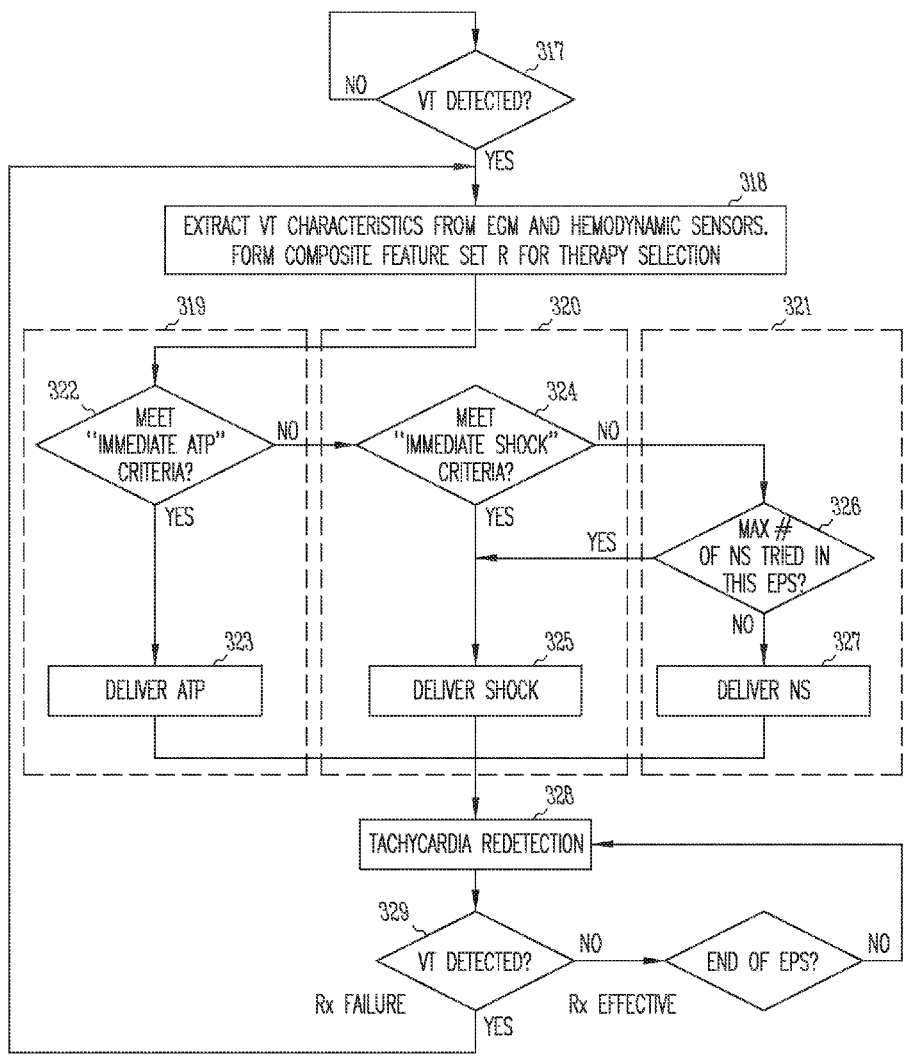
FIG. 3 illustrates an anti-tachycardia therapy, according to various embodiments of the present subject matter.

FIG. 3 illustrates an anti-tachycardia therapy, according to various embodiments of the present subject matter. At 317, it is determined whether a tachycardia is detected. If a tachycardia is detected, the process proceeds to 318 where a composite feature set R for VT therapy selection is formed. For example, VT characteristics can be extracted from the electrogram (EGM) and hemodynamic sensors. The composite features are mapped to tachycardia therapies. Thus, based on the composite feature set R, the process proceeds to deliver ATP therapy at 319, deliver shock therapy at 320, or deliver neural stimulation at 321. In the illustrated process, for example, it can be determined at 322 whether the composite feature set R meets the criteria for immediate application of ATP therapy, and if so deliver ATP therapy at 323. If not, it can be determined at 324 whether the composite feature set R meets the criteria for immediately applying a shock, and if so deliver the shock therapy at 325. If not, it can be determined at 326 whether the maximum number of neural stimulation attempts for this tachycardia episode has been made, and if so a shock can be delivered at 325. If not, neural stimulation is applied at 327. One of ordinary skill will understand, upon reading and comprehending this disclosure, that the order of these determinations can be varied, such that it is determined whether the feature set satisfies the shock criteria before the ATP criteria. Additionally, one of ordinary skill in the art will understand that a mapping function can be used to directly deliver ATP at 323 when certain criteria are met, to directly deliver a shock at 325 when other criteria are met, and deliver neural stimulation at 321 when yet other criteria are met. At 328, it is determined whether the tachycardia episode continues. If a VT is detected at 329, the process returns to 318 to form the composite feature set characteristic of the detected VT. If a VT is not detected at 329, it is determined that the therapy has been successful and the VT episode has been terminated.

Device Embodiments

Figure 4:
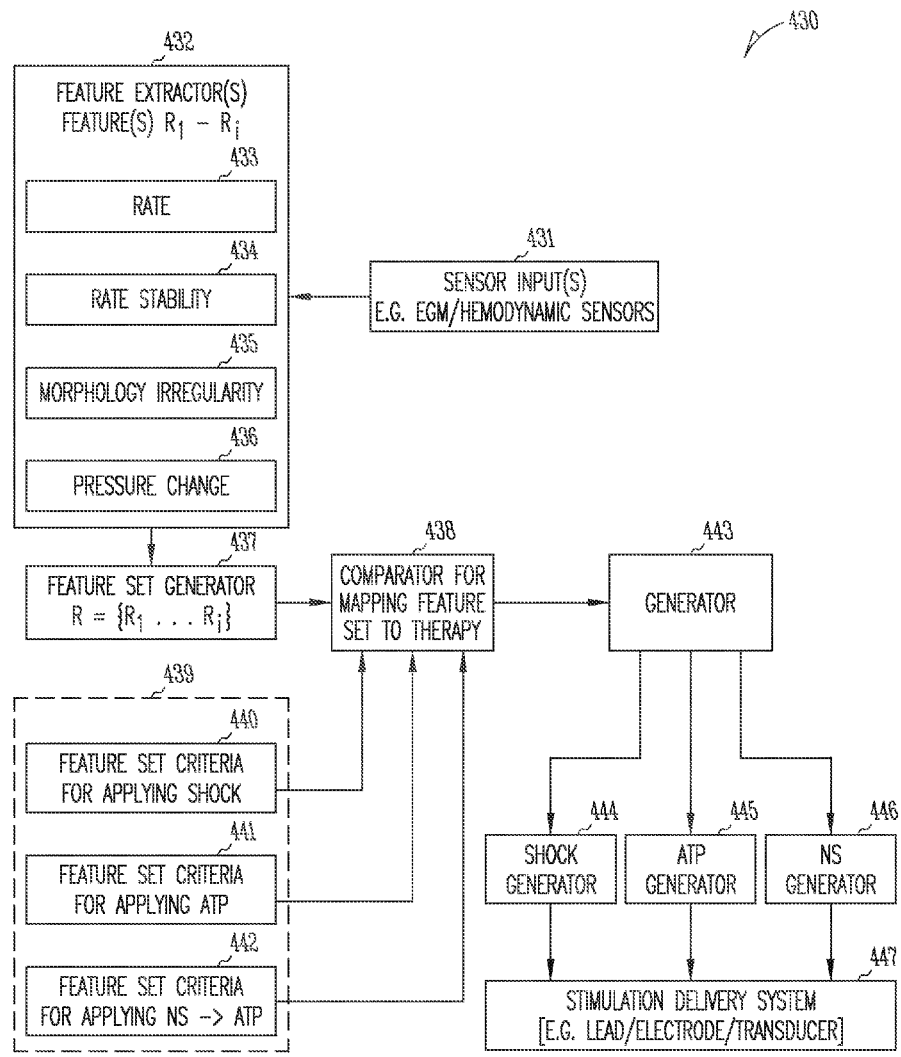
FIG. 4 illustrates an implantable medical device, according to various embodiments of the present subject matter.

FIG. 4 illustrates an implantable medical device, according to various embodiments of the present subject matter. The illustrated device 430 includes sensor inputs 431, such as EGM or hemodynamic sensors, for example. The sensors can be connected to the sensor inputs via leads or wireless channels. The sensors can also be used to determine when a tachyarrhythmia is detected. Feature extractor(s) 432 are connected to the sensor inputs 431, to extract a number of sensed features associated with the tachyarrhythmia. By way of example and not limitation, the feature extractor(s) can detect a heart rate 433, heart rate stability 434, morphology irregularity 435 and pressure change 436. A feature set generator 437 connected to the feature extractor(s) forms a composite feature set from the extracted features. A comparator 438 compares the generated feature set to feature set criteria 439. The illustrated feature set criteria includes criteria for applying shock 440, criteria for applying ATP 441, and criteria for applying neural stimulation to condition the tachyarrhythmia for ATP therapy 442. A controller 443 receives a signal from the comparator 438, and appropriately controls a shock generator 444, an ATP generator 445, and/or a NS generator 446 based on the comparison of the generated feature set to the feature set criteria. The shock generator 444, ATP generator 445 and NS generator 446 are connected to a stimulation delivery system 447 for use to deliver the shock therapy, the ATP therapy, and the neural stimulation therapy. Some of these therapies may use common electrodes, according to various embodiments. In some embodiments, these therapies use separate electrodes.

Figure 5:
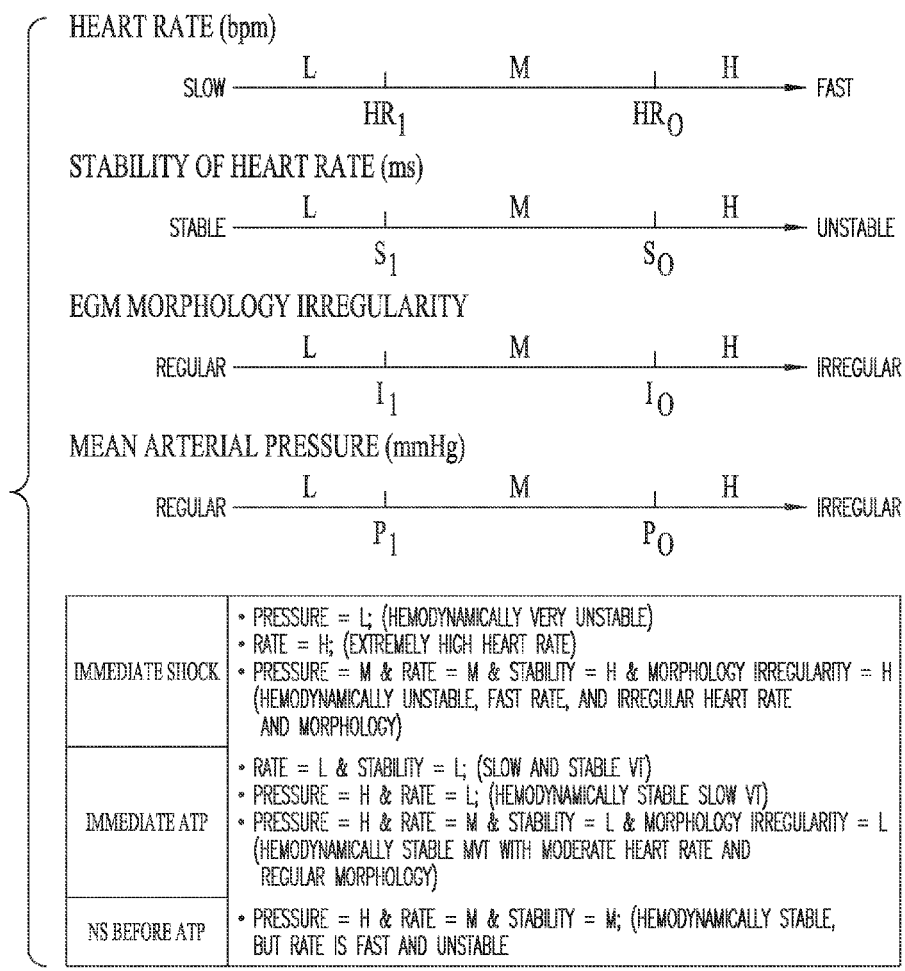
FIG. 5 illustrates criteria for use in determining whether to deliver a shock therapy, an anti-tachycardia pacing (ATP) therapy, or an ATP therapy with neural stimulation to precondition the arrhythmia, according to various embodiments of the present subject matter.

FIG. 5 illustrates criteria for use in determining whether to deliver a shock therapy, an anti-tachycardia pacing (ATP) therapy, or an ATP therapy with neural stimulation to precondition the arrhythmia, according to various embodiments of the present subject matter. According to various embodiments, when a VT is detected (e.g. a sustained rhythm within a rate zone), an N-dimensional feature set is constructed, where $R=\{R_1, R_2 \ldots, R_N\}$. Each element $R_i$ in the R set is a feature extracted either from electrical signals such as an EGM, or from the signals recorded by one or more sensors such as an accelerometer, a pressure sensor, an impedance sensor and the like. The features from these sensor signals are measures or estimates of the hemodynamic stability during the VT. In one embodiment, the R set is constructed as follows: $R=\{R_1, R_2, R_3, R_4\}$ where $R_1$ is the atrial or ventricular heart rate measured by using the rate-sensing channel in the device, $R_2$ is the stability of the rate computed as the variance of the most recent AA or RR intervals, $R_3$ is the intracardiac morphology irregularity computed as the sample entropy of the most recent heart beat morphologies, and $R_4$ is the intraventricular pressure difference from the normal condition (e.g. during normal sinus control) measured by using a dedicated implantable pulmonary arterial pressure sensor.

In some embodiments, the pressure is indirectly estimated using other sensors that measure, for example, transthoracic impedance variation, S1 and/or S2 heart sound strength variation, and the like. The composite features in R are mapped to one of the following decisions: "Deliver ATP"; "Deliver Shock"; and "Deliver NS". In various embodiments, the mapping is implemented as a set of algorithms in a processor or controller. In various embodiments, the mapping is performed using a lookup table. In various embodiments, the mapping is performed by logic circuitry.

When the feature set indicates that the tachyarrhythmia is characterized by significantly unstable hemodynamics, very fast heart rate, or very unstable rhythms in both rate and morphology, a shock therapy is delivered immediately or nearly immediately within the capabilities of the system. When the feature set indicates that the tachyarrhythmia is characterized by slow and hemodynamically stable monomorphic VTs, an ATP therapy is delivered immediately or nearly immediately within the capabilities of the system. Such rhythms are slow and hemodynamically stable monomorphic VTs. When the feature set indicates that the tachyarrhythmia is characterized by moderately fast rate, unstable rhythm, and modest hemodynamic compromise, a NS therapy is applied. Although the neural stimulation may terminate the tachyarrhythmia, the NS therapy is applied to condition the tachyarrhythmia to reduce the rate and increase the stability of the arrhythmia such that the modified tachyarrhythmia can be classified as being amendable to ATP therapy, and the corresponding feature set triggers the ATP therapy. Thus, the VT can be terminated by a preconditioning NS therapy followed by an ATP therapy rather than shock therapy as it would have been delivered in traditional ICD. In one embodiment, this mapping is implemented as a "rule base" where composite rules are used to make therapy decisions in the N-dimensional feature space.

In various embodiments, for example, shock therapy can be delivered for any of the following conditions: the pressure is less than a predetermined value indicating that the tachyarrhythmia is hemodynamically very unstable; the rate is greater than a predetermined value indicating that the tachyarrhythmia is associated with an extremely high heart rate; and the pressure is within a predetermined range of pressures, the rate is within a predetermined range of rates, the stability is higher than a threshold, and the morphology is higher than a threshold indicating that the tachyarrhythmia is hemodynamically unstable, is fast, and has an irregular heart rate and morphology.

In various embodiments, for example, ATP therapy is delivered for any of the following conditions: the rate is within a predetermined range, and the stability is less than a threshold indicating that the tachycardia is a slow and stable VT; the pressure is greater than a threshold and the rate is less than a threshold indicating a hemodynamically stable and slow VT; and the pressure is greater than a threshold, the heart rate is within a predetermined range and the stability is less than a threshold, and the morphology irregularity is less than a threshold indicating hemodynamically stable VT with moderate heart rate.

In various embodiments, for example, NS therapy is delivered when the pressure is greater than a threshold, the heart rate is within a predetermined range, and the stability is within a predetermined range indicate that the tachyarrhythmia is hemodynamically stable but the rate is fast and unstable.

Various embodiments use a decision fusion method to determine whether to apply shock, ATP or NS therapy. An example of a fusion engine function is provided by $X=f(R_1, R_2, \ldots, R_N)$. In one example, $R_i$ is defined such that a larger $R_i$ indicates severer condition; and $f$ is a linear function of all $R_i$ such that X is the weighted sum of all features R. The weight k is the risk factor. Then, for example, shock can be delivered if X is greater than a first threshold, ATP therapy can be delivered if X is less than a second threshold, and NS therapy can be delivered if X is between the first and second thresholds.

According to some embodiments, a number of NS protocols with different settings (such as the frequency, duration, etc. are preprogrammed and stored in the device. In one embodiment, heart rate variability (HRV) is monitored before and during VT to determine which NS protocol to use when "Deliver NS" decision is made. Standard HRV parameters (e.g. SDANN in time domain, or LF/HF ratio in frequency domain) are quantities to describe sympathetic/paraspathetic balance. Other methods for determining autonomic balance or health, such as heart rate turbulence (HRT) or neural sensors, can be used. A significant autonomic imbalance may require more aggressive NS therapy. The selection of an appropriate NS protocol can be also based on the time of the day. As VT occurrence follows a circadian rhythm (significantly higher rate of VT occurrence and ATP failure happens between 6 a.m. to 12 p.m.), a more aggressive NS therapy can be applied during this period of increased VT risk.

The neural stimulation can be applied to a vagus nerve, a cardiac branch of the vagus nerve, a cardiac fat pad, a baroreceptor site, or to other neural targets that stimulate the parasympathetic nervous system or inhibit the sympathetic nervous system. The neural stimulation can be applied using intravascularly-fed electrodes, nerve cuffs, satellite electrodes, and other known means for stimulating a neural target.

The application of NS therapy before ATP therapy can be useful in terminating a broader spectrum of VTs that would have been shocked in conventional ICDs, due to their fast rate, unstable rhythms, or hemodynamic compromise. The efficacy of painless therapy may be greatly improved and the painful shock therapy be reduced.

Figure 6:
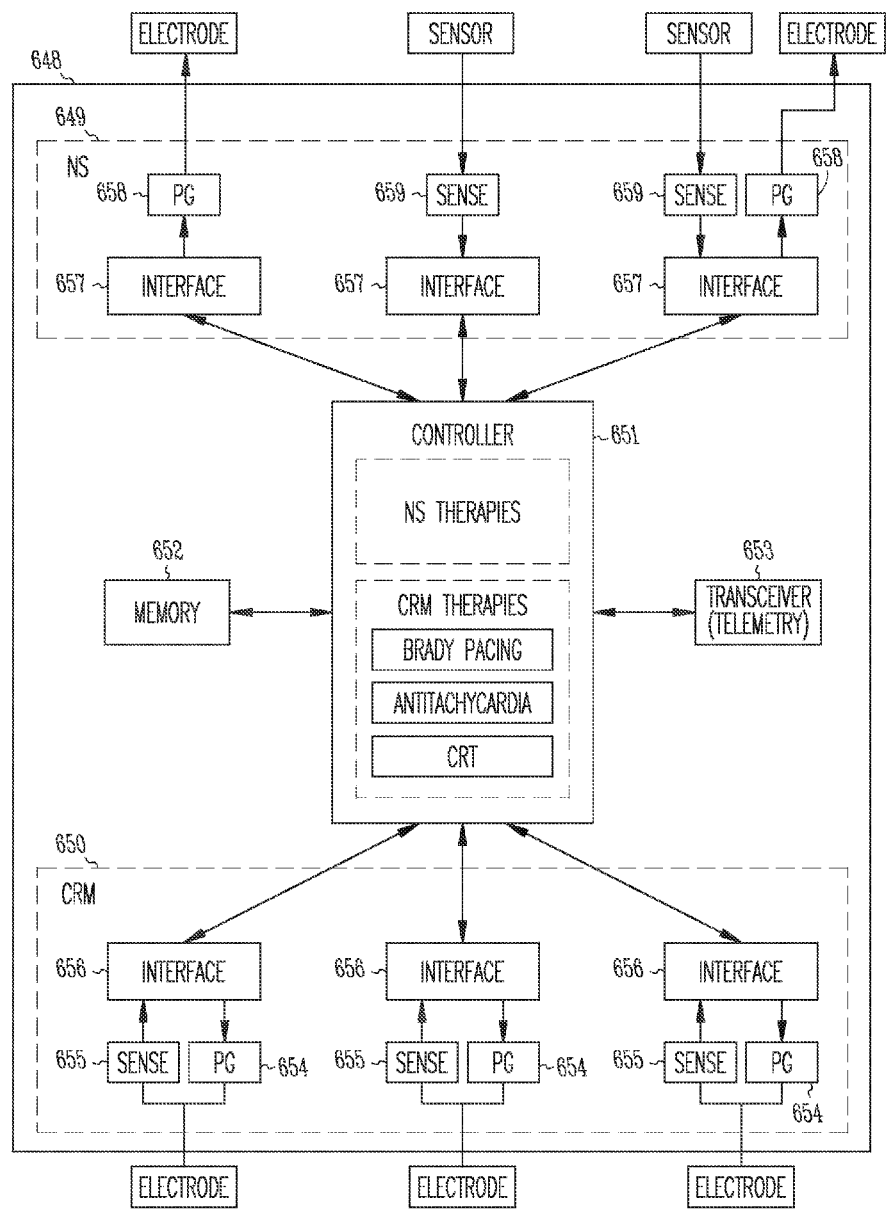
FIG. 6 illustrates an implantable medical device (IMD) having a neural stimulation (NS) component and cardiac rhythm management (CRM) component, according to various embodiments of the present subject matter.

FIG. 6 illustrates an implantable medical device (IMD) 648 having a neural stimulation (NS) component 649 and cardiac rhythm management (CRM) component 650, according to various embodiments of the present subject matter. The illustrated device includes a controller 651 and memory 652. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CPA functions. Examples of CRM functions include bradycardia pacing, anti-tachycardia therapies such as ATP, defibrillation and cardioversion, and CRT. The controller also executes instructions to detect a tachyarrhythmia. The illustrated device further includes a transceiver 653 and associated circuitry for use to communicate with a programmer or another external or internal device. Various embodiments include a telemetry coil.

The CRM therapy section 650 includes components, under the control of the controller, to stimulate a heart and/or sense cardiac signals using one or more electrodes. The illustrated CRM therapy section includes a pulse generator 654 for use to provide an electrical signal through an electrode to stimulate a heart, and further includes sense circuitry 655 to detect and process sensed cardiac signals. An interface 656 is generally illustrated for use to communicate between the controller 651 and the pulse generator 654 and sense circuitry 655. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 649 includes components, under the control of the controller, to stimulate a neural stimulation target and/or sense parameters associated with nerve activity or surrogates of nerve activity such as blood pressure and respiration. Three interfaces 657 are illustrated for use to provide neural stimulation. However, the present subject matter is not limited to a particular number interfaces, or to any particular stimulating or sensing functions. Pulse generators 658 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 659 are used to detect and process signals from a sensor, such as a sensor of nerve activity, blood pressure, respiration, and the like. The interfaces 657 are generally illustrated for use to communicate between the controller 651 and the pulse generator 658 and sense circuitry 659. Each interface, for example, may be used to control a separate lead. Various embodiments of the NS therapy section only includes a pulse generator to stimulate neural targets such a vagus nerve.

Figure 7:
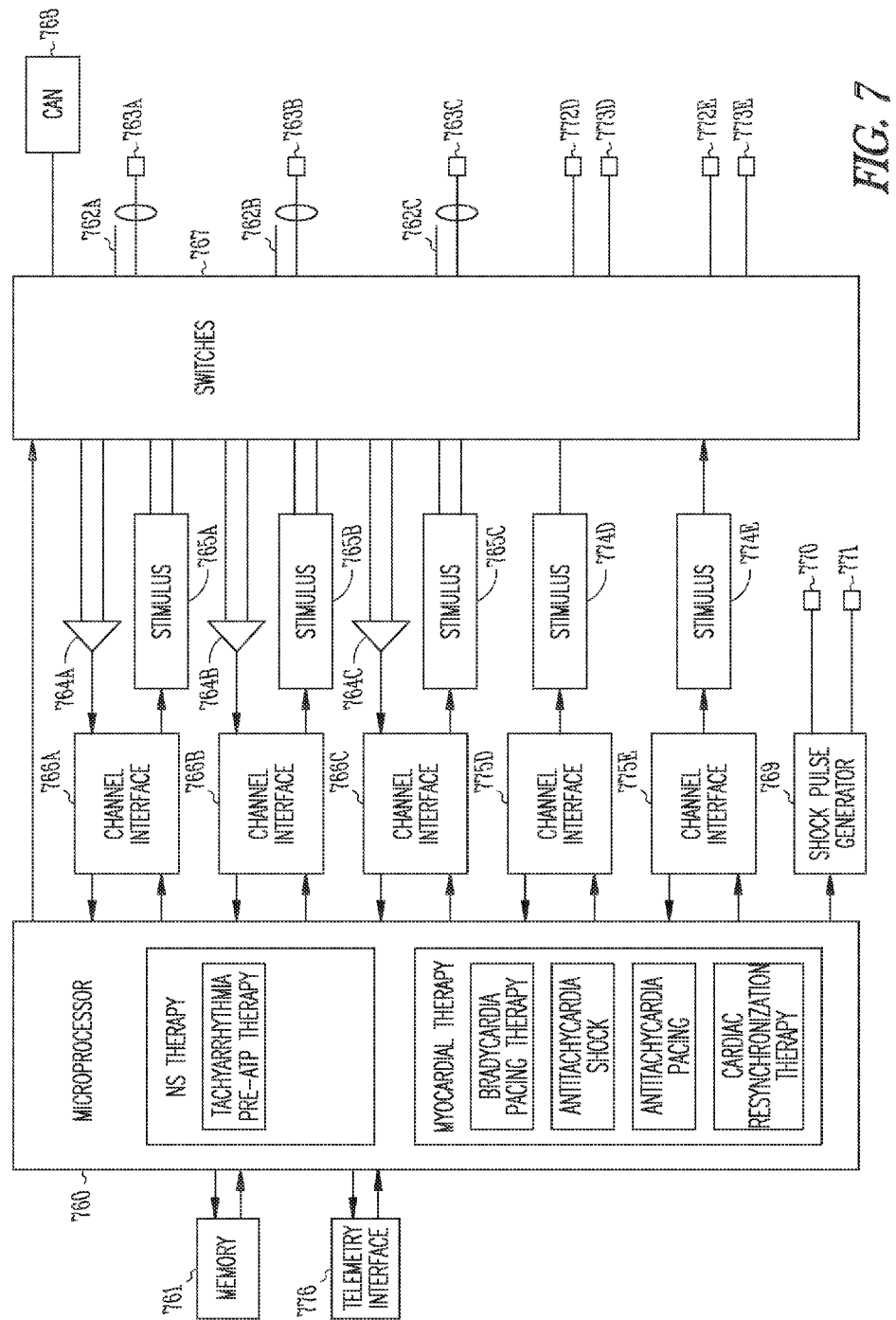
FIG. 7 shows a system diagram of an embodiment of a microprocessor-based implantable device, according to various embodiments.

FIG. 7 shows a system diagram of an embodiment of a microprocessor-based implantable device, according to various embodiments. The controller of the device is a microprocessor 760 which communicates with a memory 761 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 762A-C and tip electrodes 763A-C, sensing amplifiers 764A-C, pulse generators 765A-C, and channel interfaces 766A-C. Each channel thus includes a pacing channel made up of the pulse generator connected to the electrode and a sensing channel made up of the sense amplifier connected to the electrode. The channel interfaces 766A-C communicate bidirectionally with microprocessor 760, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 767 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 768 or an electrode on another lead serving as a ground electrode. A shock pulse generator 769 is also interfaced to the controller for delivering a defibrillation shock via a pair of shock electrodes 770 and 771 to the atria or ventricles upon detection of a shockable tachyarrhythmia.

The controller may be programmed with a plurality of selectable ATP pacing protocols that define the manner in which anti-tachycardia pacing is delivered. In a microprocessor-based device, the output of pacing pulses can be controlled by a pacing routine that implements the selected pacing protocol as defined by various parameters. A data structure stored in memory contains the parameter sets that define each of the available pacing protocols. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy.

Neural stimulation channels, identified as channels D and E, are incorporated into the device for delivering parasympathetic stimulation and/or sympathetic inhibition, where one channel includes a bipolar lead with a first electrode 772D and a second electrode 773D, a pulse generator 774D, and a channel interface 775D, and the other channel includes a bipolar lead with a first electrode 772E and a second electrode 773E, a pulse generator 774E, and a channel interface 775E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate stimulation site, e.g., near a baroreceptor in the case of a sympathetic inhibition channel or near a parasympathetic nerve in the case of a parasympathetic stimulation channel. Other types of leads and/or electrodes may also be employed. A nerve cuff electrode may be used in place of an intravascularly disposed electrode to provide neural stimulation, where the electrode may be placed, for example, around the cervical vagus nerve bundle to provide parasympathetic stimulation or around the aortic or carotid sinus nerve to provide sympathetic inhibition. Baroreceptors in or near the pulmonary artery may also be stimulated. In another embodiment, the leads of the neural stimulation electrodes are replaced by wireless links, and the electrodes for providing parasympathetic stimulation and/or sympathetic inhibition are incorporated into satellite units. Although the applied neural stimulation may terminate a tachyarrhythmia, the neural stimulation is expected to change the tachycardia into a rhythm that has a high likelihood of being successfully terminated by ATP.

The figure illustrates a telemetry interface 776 connected to the microprocessor, which can be used to communicate with an external device. The illustrated microprocessor 760 is capable of performing neural stimulation therapy routines and myocardial stimulation routines. Examples of NS therapy routines include a pre-ATP NS therapy for a tachyarrhythmia. Examples of myocardial therapy routines include bradycardia pacing therapies, anti-tachycardia shock therapies such as cardioversion or defibrillation therapies, anti-tachycardia pacing therapies, and cardiac resynchronization therapies.

System Embodiments

Figure 8:
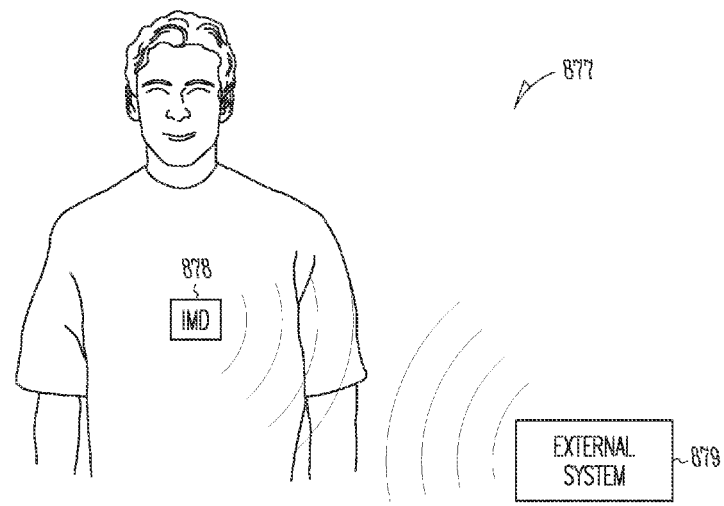
FIG. 8 illustrates a system including an implantable medical device (IMD) and an external system or device, according to various embodiments of the present subject matter.

FIG. 8 illustrates a system 877 including an implantable medical device (IMD) 878 and an external system or device 879, according to various embodiments of the present subject matter. Various embodiments of the IMD 878 include a combination of NS and CRM functions. The IUD may also deliver biological agents and pharmaceutical agents. The external system 879 and the IMD 878 are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates a neural target and/or myocardium to provide an anti-tachycardia therapy.

The external system allows a user such as a physician or other caregiver or a patient to control the operation of IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to IMD. This includes, for example, programming the IMD to acquire physiological data, programming IMD to perform at least one self-diagnostic test (such as for a device operational status), and programming the IMD to deliver at least one therapy.

Figure 9:
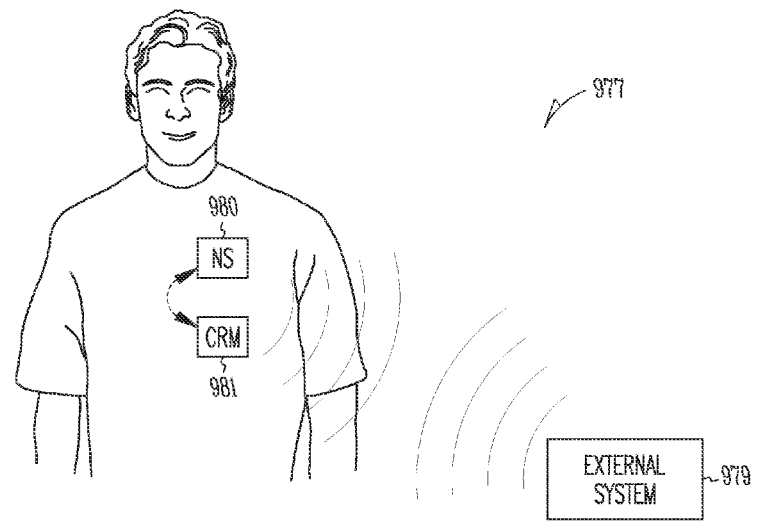
FIG. 9 illustrates a system including an external device, an implantable neural stimulator (NS) device and an implantable cardiac rhythm management (CRM) device, according to various embodiments of the present subject matter.

FIG. 9 illustrates a system 977 including an external device 979, an implantable neural stimulator (NS) device 980 and an implantable cardiac rhythm management (CRM) device 981, according to various embodiments of the present subject matter. Various aspects involve a method for communicating between an NS device and a CRM device or other cardiac stimulator. In various embodiments, this communication allows one of the devices 980 or 981 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

Figure 10:
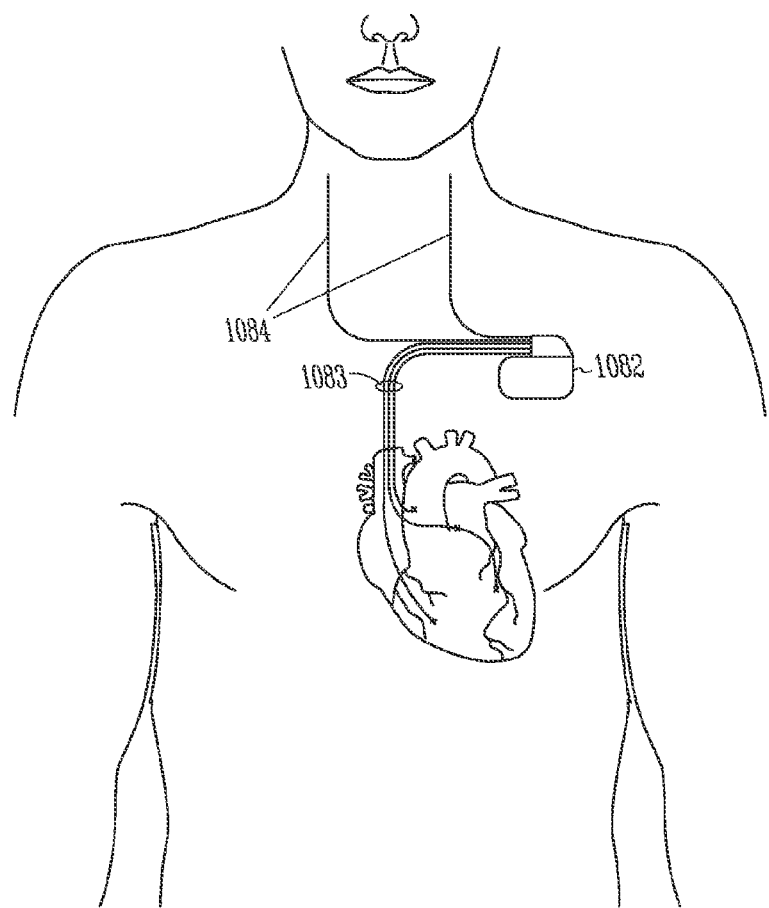
FIG. 10 illustrates an IMD placed subcutaneously or submuscularly in a patient's chest with lead(s) positioned to provide a CRM therapy to a heart, and with lead(s) positioned to stimulate a vagus nerve, by way of example and not by way of limitation, according to various embodiments.

FIG. 10 illustrates an IMD 1082 placed subcutaneously or submuscularly in a patient's chest with leaks) 1083 positioned to provide a CRM therapy to a heart, and with lead(s) 1084 positioned to stimulate a vagus nerve, by way of example and not by way of limitation, according to various embodiments. The leads 1083 can be used to deliver ATP and/or shock therapy. According to various embodiments, the leads 1083 are positioned in or proximate to the heart to provide a desired cardiac pacing therapy. In some embodiments, the lead(s) 1083 are positioned in or proximate to the heart to provide a desired CRT therapy. Some embodiments place the leads in positions with respect to the heart that enable the lead(s) to deliver the combinations of at least two of the pacing, defibrillation and CRT therapies. According to various embodiments, neural stimulation lead(s) 1084 are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments stimulate the vagus nerve using electrode(s) positioned within the internal jugular vein.

Figure 11:
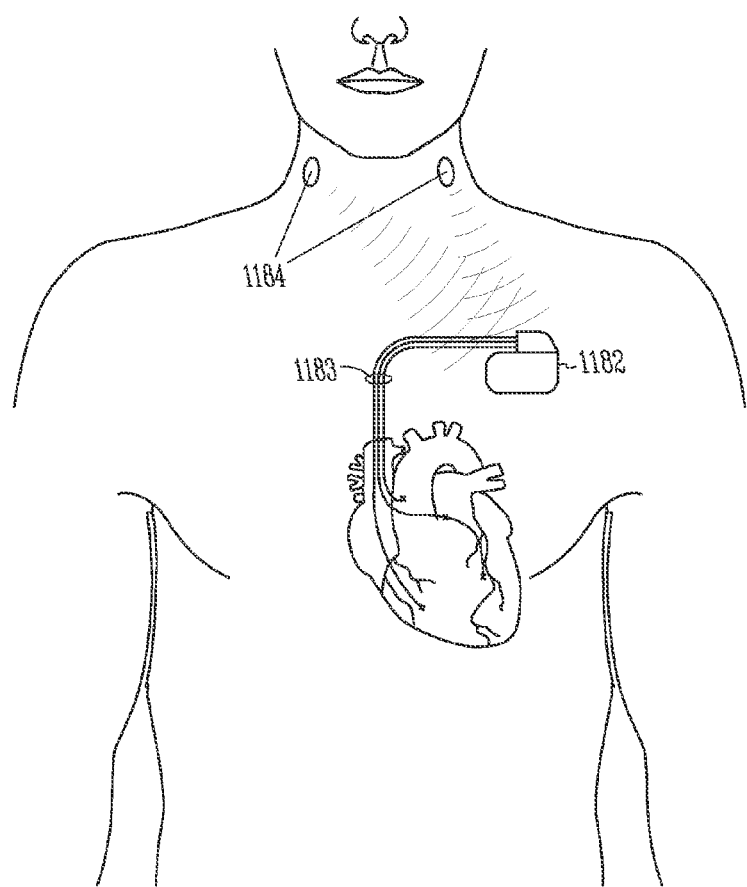
FIG. 11 illustrates an IMD with lead(s) positioned to provide a CRM therapy to a heart, and with satellite transducers positioned to stimulate at least one parasympathetic neural target as part of a myocardium conditioning therapy, according to various embodiments.

FIG. 11 illustrates an IMD 1182 with lead(s) 1183 positioned to provide a CRM therapy to a heart, and with satellite transducers 1184 positioned to stimulate at least one parasympathetic neural target as part of a myocardium conditioning therapy, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous transducers, nerve cuff transducers and intravascular transducers.

Figure 12:
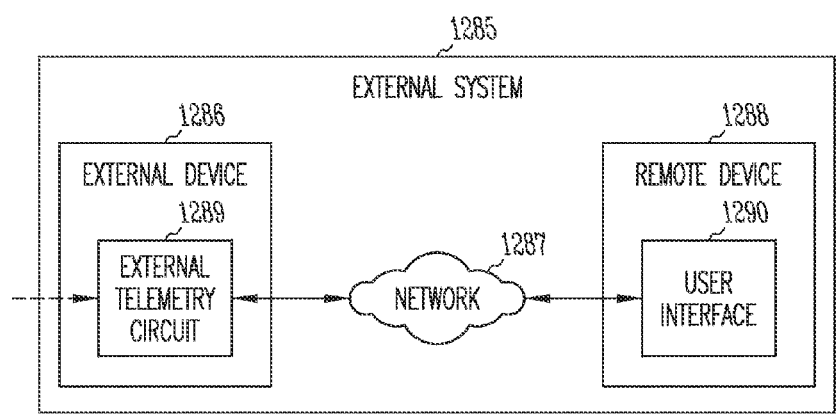
FIG. 12 is a block diagram illustrating an embodiment of an external system.

FIG. 12 is a block diagram illustrating an embodiment of an external system 1285. The external system includes a programmer, in some embodiments. In the embodiment illustrated in FIG. 12, the external system includes a patient management system. As illustrated, external system 1285 is a patient management system including an external device 1286, a telecommunication network 1287, and a remote device 1288. External device 1286 is placed within the vicinity of an and includes external telemetry system 1289 to communicate with the IMD. Remote device(s) 1288 is in one or more remote locations and communicates with external device 1286 through network 1287, thus allowing a physician or other caregiver to monitor and treat a patient from a distant location and/or allowing access to various treatment resources from the one or more remote locations. The illustrated remote device 1288 includes a user interface 1290.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system, comprising:
   at least one sensor input adapted to receive at least one sensed signal associated with a tachyarrhythmia;
   a feature set extractor adapted to extract at least two features from the at least one sensed signal associated with the tachyarrhythmia;
   a feature set generator adapted to form a feature set using the at least two features extracted by the feature set extractor;
   at least one generator adapted for use to selectively apply a shock therapy, an anti-tachycardia pacing (ATP) therapy, and a neural stimulation (NS) therapy; and
   a controller adapted to respond to the feature set, the controller being adapted to initiate the shock therapy when the feature set corresponds to criteria for applying the shock therapy, initiate the ATP therapy when the feature set corresponds to criteria for applying the ATP therapy, and initiate the NS therapy when the feature set corresponds to criteria for applying the NS therapy, wherein the controller is configured to detect a ventricular tachycardia (VT), characterize the detected VT to distinguish between a moderately fast rate and a very fast rate, distinguish between a stable rhythm and an unstable rhythm and distinguish among significantly unstable hemodynamics, stable hemodynamics, and modest hemodynamic compromise, and initiate the NS therapy when the detected VT is characterized by a combination of all of the following: a moderately fast rate, an unstable rhythm and a modest hemodynamic compromise.

2. The system of claim 1, wherein the controller is adapted to
determine if the feature set corresponds to the criteria for applying the ATP therapy, then determine if the feature set corresponds to the criteria for applying the shock therapy if the feature set did not correspond to the ATP therapy.

3. The system of claim 1, wherein the at least one sensor input includes an input to receive an electrogram (EGM) signal.

4. The system of claim 1, wherein the at least one sensor input includes an input to receive a signal from a hemodynamic sensor.

5. The system of claim 1, wherein the at least two features are selected from a heart rate, a stability of the heart rate, an irregularity of an electrogram morphology, or a pressure.

6. The system of claim 1, wherein the NS therapy is adapted to modify the tachyarrhythmia to be amenable to the ATP therapy, the feature set extractor is adapted to extract features from the modified tachyarrhythmia, the feature set generator is adapted to form a corresponding feature set for the modified tachyarrhythmia, and the controller is adapted to initiate the ATP therapy when the feature set for the modified tachyarrhythmia corresponds to criteria for applying the ATP therapy.

7. The system of claim 1, wherein the controller is adapted to use the feature set generator to construct the feature set in response to the detected VT.

8. The system of claim 7, wherein:
the NS therapy is initiated to modify the detected VT when the detected VT is characterized by a moderately fast rate, an unstable rhythm and a modest hemodynamic compromise; and
initiate the ATP therapy to terminate the modified VT.

9. The system of claim 1, wherein the controller is adapted to use the feature set generator to construct the feature set in response to the detected VT,
wherein the criteria for applying the NS therapy includes criteria to modify the detected VT, the criteria including: the pressure is higher than a first pressure threshold, the heart rate is higher than a first heart rate threshold and lower than a second heart rate threshold, and the heart rate stability is higher than a first threshold and lower than a second threshold.

10. The system of claim 1, further comprising at least one electrode adapted to stimulate a vagus nerve, wherein the NS therapy includes vagus nerve stimulation therapy.

11. The system of claim 10, wherein the electrode includes an intravascularly-fed electrode adapted fur use in transvascularly stimulating the vagus nerve from an internal jugular vein.

12. The system of claim 10, wherein the electrode includes a subcutaneously-fed lead nerve cuff electrode adapted for use in stimulating the vagus nerve.

13. A system, comprising:
means for receiving at least one sensed signal associated with a tachyarrhythmia;
means for extracting at least two features from the at least one sensed signal associated with the tachyarrhythmia and forming a feature set using the at least two features;
means for providing a shock therapy when the feature set corresponds to criteria for applying the shock therapy;
means for providing an anti-tachycardia pacing (ATP) therapy when the feature set corresponds to criteria for applying the ATP therapy; and
means for providing a neural stimulation (NS) therapy when the feature set corresponds to criteria for applying the NS therapy to modify the tachyarrhythmia to be amenable to the ATP therapy, wherein the means for providing the NS therapy is configured to detect a ventricular tachycardia (VT), characterize the detected VT to distinguish between a moderately fast rate and a very fast rate, distinguish between a stable rhythm and an unstable rhythm, and distinguish among significantly unstable hemodynamics, stable hemodynamics, and modest hemodynamic compromise, and initiate the NS therapy when the detected VT is characterized by a combination of all of the following: a moderately fast rate, an unstable rhythm and a modest hemodynamic compromise.

14. The system of claim 13, wherein the means for receiving at least one sensed signal associated with the tachyarrhythmia includes means for receiving a heart rate value, a heart rate stability value, a regularity value for an electrogram morphology, and pressure value.

15. A method, comprising:
receiving from at least one sensor at least one sensed signal associated with a tachyarrhythmia;
extracting at least two features from the at least one sensed signal associated with the tachyarrhythmia and forming a feature set using the at least two features;
providing a shock therapy when the feature set corresponds to criteria for applying the shock therapy;
providing an anti-tachycardia pacing (ATP) therapy when the feature set corresponds to criteria for applying the ATP therapy; and
providing a neural stimulation (NS) therapy when the feature set corresponds to criteria for applying the NS therapy to modify the tachyarrhythmia to be amenable to the ATP therapy,
wherein the shock therapy, the ATP therapy, and the NS therapy are provided using at least one generator;
wherein providing the NS therapy includes using a controller to:
detect a ventricular tachycardia (VT),
characterize the detected VT to distinguish between a moderately fast rate and a very fast rate, distinguish between a stable rhythm and an unstable rhythm, and
distinguish among significantly unstable hemodynamics, stable hemodynamics, and modest hemodynamic compromise, and
initiate the NS therapy when the detected VT is characterized by a combination of all of the following: a moderately fast rate, an unstable rhythm and a modest hemodynamic compromise.

16. The method of claim 15, wherein receiving at east one sensed signal associated with the tachyarrhythmia includes receiving a heart rate value, a heart rate stability value, a regularity value for an electrogram morphology, and pressure value.

17. The method of claim 15, wherein the criteria for applying the shock therapy includes:
criteria that indicates the tachyarrhythmia is hemodynamically unstable above a higher unstability threshold value;
criteria that indicates the tachyarrhythmia has a heart rate above a higher rate threshold; or
criteria that indicates the tachyarrhythmia is hemodynamically unstable above a lower unstability threshold value and below the higher unstability value, that indicates the tachyarrhythmia has a heart rate above a lower rate threshold and below the higher unstability value, and indicates that the tachyarrhythmia has an irregular heart rate and morphology.

18. The method of claim 15, wherein the criteria for applying the ATP therapy includes:
   criteria that indicates the tachyarrhythmia is slow and stable;
   criteria that indicates the tachyarrhythmia is hemodynamically stable and slow; or
   criteria that indicates the tachyarrhythmia is hemodynamically stable and has a moderate rate and a regular morphology.

19. The method of claim 15, wherein the criteria for applying neural stimulation includes criteria that indicates the tachyarrhythmia is hemodynamically stable and has a fast and unstable rate.

20. The method of claim 15, further comprising:
   detecting a ventricular tachycardia (VT);
   constructing the feature set in response to the detected VT;
   initiating the NS therapy to modify the detected VT when the detected VT is characterized by a moderately fast rate, an unstable rhythm and a modest hemodynamic compromise; and
   initiating the ATP therapy to terminate the modified VT.

* * * * *